United States Patent
Sumanaweera et al.

(10) Patent No.: US 6,306,091 B1
(45) Date of Patent: Oct. 23, 2001

(54) DIAGNOSTIC MEDICAL ULTRASOUND SYSTEMS AND METHODS UTILIZING ESTIMATION OF 3-DIMENSIONAL RIGID BODY TRANSFORMATION

(75) Inventors: Thilaka S. Sumanaweera, San Jose; John A. Hossack, Palo Alto, both of CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/369,824

(22) Filed: Aug. 6, 1999

(51) Int. Cl.[7] ............................................. A61B 8/00
(52) U.S. Cl. ................................ 600/443; 128/916
(58) Field of Search ............................. 600/437, 443, 600/447, 407, 409, 414; 128/916; 382/130–132, 209, 216, 276, 293–297

(56) References Cited

U.S. PATENT DOCUMENTS

| | | | |
|---|---|---|---|
| 5,655,535 | 8/1997 | Friemel et al. | 128/660.07 |
| 5,776,067 | * 7/1998 | Kamada et al. | 600/443 |
| 5,871,013 | * 2/1999 | Wainen et al. | 600/407 |
| 5,899,861 | 5/1999 | Friemel et al. | 600/443 |
| 5,910,114 | 6/1999 | Nock et al. | 600/437 |
| 6,064,904 | * 5/2000 | Yanof et al. | 600/414 |
| 6,106,466 | * 8/2000 | Sheehan et al. | 600/443 |
| 6,126,600 | * 10/2000 | Oxaal et al. | 600/443 |

FOREIGN PATENT DOCUMENTS

WO 98/25509  6/1998  (WO).

OTHER PUBLICATIONS

J. A. Hossack, J. W. Sliwa, S. H. Maslak, E.A. Gardner, G.L. Holley, and D. J. Napolitano, "Multiple Ultrasound Image Registration System, Method and Transducer."

J. D. Foley, A. van Dam, S.K. Feiner, and J. F. Hughes, eds., "Computer Graphics: Principles and Practive." New York: Addison–Wesley, 1990.

B. K. P. Horn, "Closed–Form Solution of Absolute Orientation Using Unit Quaternions," Journal of Optical Society of America A, vol. 4, pp. 629–642, Apr. 1987.

K. S. Arun, T.S. Huang, and S. D. Blostein, "Least–Squares Fitting of Two 3D Point Sets," IEEE Transactions on Pattern Analysis and Machine Intelligence, vol. PAMI–9, No. 5, pp. 698–700, 1987.

B.K.P. Horn, H. M. Hilden, and S. Negahdaripour, "Closed–Form Solution of Absolute Orientation Using Orthonormal Matrices," Journal of Optical Society of America A, vol. 5, pp. 1127–1135, Jul. 1988.

J. M. Fitzpatrick, J.B. West, and C.R. Maurer, "Predicting Error in Rigid–Body Point–Based Registration," IEEE Transactions on Medical Imaging, vol. 15, pp. 694–702, Oct. 1998.

C. M. Brown, "Some Computational Properties of Rotation Representations," Technical Report 303, University of Rochester, Department of Computer Science, Aug. 23, 1989.

* cited by examiner

Primary Examiner—Francis J. Jaworski
(74) Attorney, Agent, or Firm—Brinks Hofer Gilson & Lione (57) ABSTRACT

The use of transformations in ultrasound systems is disclosed. A first set of points in a first data set or a subset of a first data set is known to correspond to a second set of points in a second data set or a subset of a second data set. The point correspondence can be established using any number of techniques including speckle and/or feature correlation, speckle decorrelation time delays. Spectral broadening, power and spectral peak. A method for estimating the best fitting rigid body transformation that maps the first data set or a subset of the first data set to the second data set or a subset of the second data set is disclosed. This yields three dimensional ultrasonic data sets which preserves the shapes of object they represent.

65 Claims, 5 Drawing Sheets

DIAGNOSTIC MEDICAL ULTRASOUND SYSTEMS AND METHODS UTILIZING ESTIMATION OF 3-DIMENSIONAL RIGID BODY TRANSFORMATION

REFERENCE TO MICROFICHE APPENDIX

A microfiche appendix is included of a computer program listing. The total number of microfiche is 1. The total number of frames is 26.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

This invention relates to medical diagnostic ultrasound systems and methods capable of constructing three-dimensional representations from disjoint two or three-dimensional image data sets of humans or animals. More particularly, this invention relates to ultrasound systems and methods which provide accurate three-dimensional reconstruction between any two ultrasonic data sets acquired by translating or rotating a transducer along one or more of the six degrees of freedom.

BACKGROUND

There is growing interest in three-dimensional ultrasonic imaging wherein a three dimensional volume is represented in two dimensions, such as on a video display. One approach to obtaining such images is to use a two-dimensional ("2D") transducer array to obtain three-dimensional image information directly. A 2D array is used to scan electronically in any desired orientation, and thereby acquire the desired information. This approach has considerable problems related to fabrication difficulties, signal to noise difficulties and processing difficulties. Further, it is sometimes desired to obtain a three-dimensional image of a volume which is larger than the scan field of the 2D transducer.

Another approach to three-dimensional imaging is to collect multiple two-dimensional image data frames using a one-dimensional ("1D") transducer array. These frames are subsequently assembled into the desired three-dimensional reconstruction using relative positional information. This approach is also used to scan multiple volumes with a 2D transducer. Multiple three-dimensional data sets are obtained and then subsequently assembled into a larger three-dimensional data set.

As the transducer is manually moved to collect the series of images, translation and rotation of the transducer may impart distortion from one image to the next. While mechanical systems have been developed to control transducer movement and image acquisition, such devices are usually cumbersome to operate and expensive to manufacture. Further, with both manual and mechanical transducer movement, perfectly aligned continuous frames of images are difficult to acquire. There are often gaps in the acquired data which represent gaps between successive frames. When the images are assembled into the three-dimensional volume, these gaps are filled by subsequent processing. To accurately fill these gaps, it is important to know the translation and rotation of the transducer and/or image plane from one image to the next.

Sensors on the transducer have been used to compute rotation and translation of the transducer to correct for the distortion. See for example "MULTIPLE ULTRASOUND IMAGE REGISTRATION SYSTEM, METHOD AND TRANSDUCER", U.S. application Ser. Nos. 08/621,561 (filed Mar. 25, 1996), 08/807,498 (filed Feb. 27, 1997) and 08/916,585 (filed Aug. 22, 1997) to Hossack et al., assigned to the assignee of the present invention and U.S. Pat. No. 5,655,535 to Friemel et al., entitled 3-DIMENSIONAL COMPOUND ULTRASOUND FIELD OF VIEW, all of which are herein incorporated by reference. These references disclose methods of collecting ultrasonic image data and estimating the local displacement of a collection of data points in each image data set Once these local displacements are calculated, the images are then registered and assembled together to generate a 3D volume.

SUMMARY

By way of introduction, the preferred embodiments described below relate to an ultrasound system and method for accurately reconstructing three-dimensional image data sets from multiple two or three-dimensional image data sets. More particularly, the presently preferred embodiments relate to an improved ultrasound system and method utilizing affine transformations which adhere to a rigid body criterion. In a first preferred embodiment, quatemions are used to perform the affine transformation. In a second preferred embodiment, orthonormal matrices are used to perform the affine transformation. The resultant three-dimensional reconstructions are rendered more quickly, are more accurate and are less likely to be deformed or skewed.

DETAILED DESCRIPTION OF THE PRESENTLY PREFERRED EMBODIMENTS

I. Overview

Figure 1:
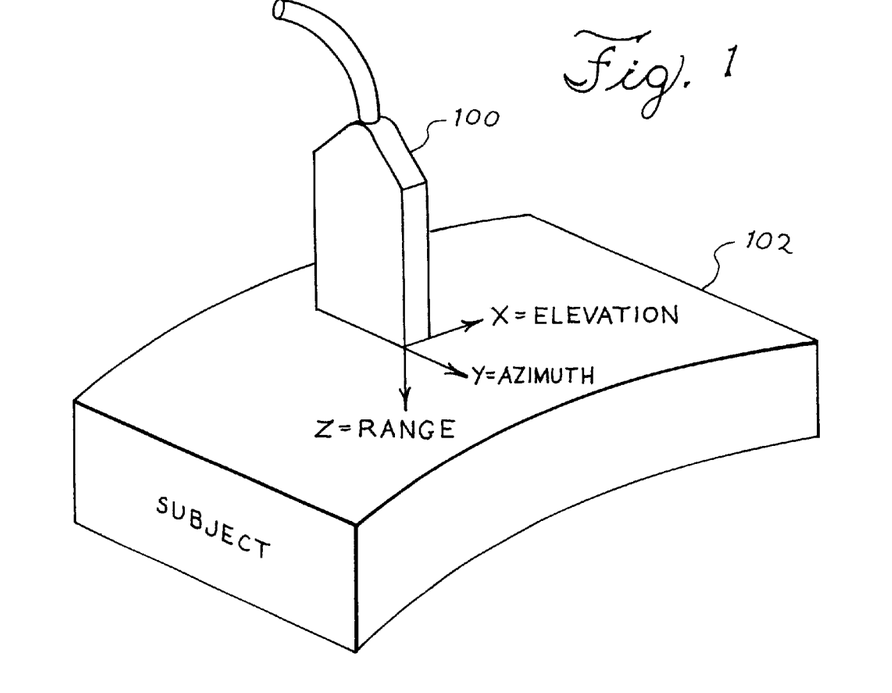
FIG. 1 depicts a perspective view of an ultrasound transducer for obtaining three-dimensional ultrasonic image data sets.

In a typical ultrasound examination session, a sonographer uses an ultrasound transducer to scan a patient. The sonographer holds the ultrasound transducer against the patient's body in a location and at an orientation which scans the desired area. When more than one image is required, such as to assemble a three dimensional volume, the sonographer moves the transducer to different places on the patient's body to acquire the desired images. Each image represents a two dimensional slice or three dimensional section through the patient's three dimensional body and organs. Herein, the word "image" is defined to include both two and three-dimensional ultrasonic image data sets. Each image includes a number of data points which make up the image and represent a particular slice/section of the three-dimensional body. Therefore the object projects out of the plane of the scan. If two slices are taken of the same three dimensional object at different places, data points in the first slice are said to be displaced to corresponding data points in the second slice, ie., there is a continuous connection between the points through the object. The local displacement for a given point describes where that point in one plane will be displaced to in a subsequent plane through the object. Local displacements can be along any arbitrary direction in three-dimensions. Referring to FIG. 1, the one dimensional transducer 100 is moved along the elevation direction of the subject 102 while acquiring a series of images. Alternatively, the transducer 100 can be held in place while the ultrasound beam is electronically swept through the subject 102, or this can be combined with moving the transducer 100. The transducer 100 can be of a conventional or specialized type. The local displacement of a collection of points from each image to the next is then estimated by any suitable technique, such as speckle and/or feature correlation, speckle decorrelation, time delays, spectral broadening, power or spectral peak.

The points for which the local displacements are calculated are selected by using a predefined criteria such as points spaced equally along the range direction, points with highest image information content or points placed by the user. Once the local displacements are estimated, the rigid body transformation that best describes the local displacements is determined. From this calculation, the rigid body transformation for any point in the image plane can be calculated.

Alternatively, the sonographer may use a two-dimensional transducer array to acquire a three-dimensional data set. A second three-dimensional data set is acquired from a different view by moving or sweeping the transducer in an arbitrary fashion. The displacement of points from the first data set to the second data set can then be estimated using the above techniques. Once the local displacements are computed, the rigid body transformation between the two data sets can also be found using the techniques disclosed herein.

Figure 2:
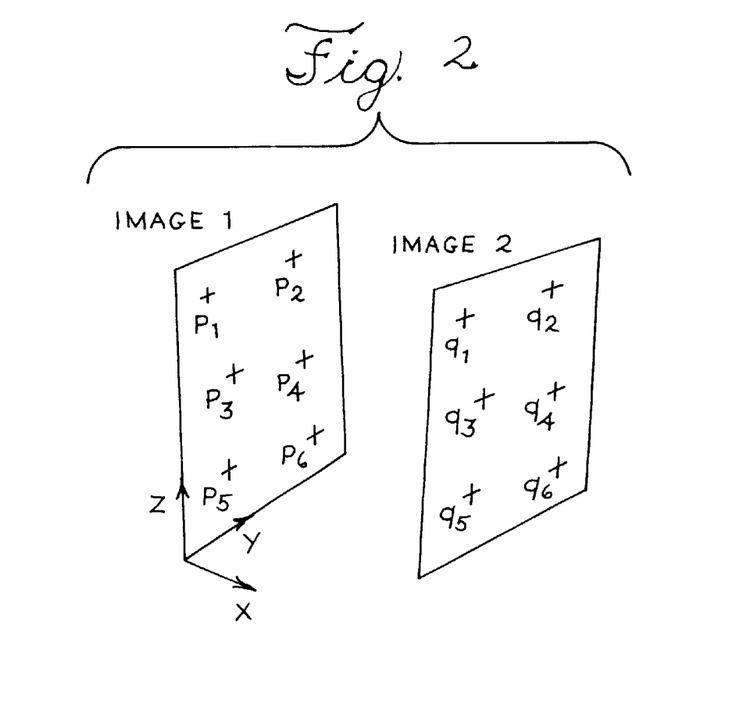
FIG. 2 depicts two representative image planes obtained within the volume of FIG. 1.

FIG. 2 shows a pair of two dimensional images, 1 and 2, in a series of images acquired by moving the transducer 100 as described above and shown in FIG. 1. Points $p_i$ (i=0 . . . N−1) in image 1 are estimated to be displaced to points $q_i$ (i=0 . . . N−1) in image 2. Points $p_i$ and $q_i$ can be substantially close to one another or substantially far apart, i.e. the image misalignment can range from very small to very large. These points were selected by using the predefined criteria that the points be spaced equally along the range direction. Alternatively, criteria such as points with highest image information content or points placed by the user can also be used. The transformation between the images 1 and 2 is found that minimizes the least squared error between points.

One solution to this problem is as follows:

1. For each point, find the displacement from the first image to the second image: $d_i = p_i - q_i$ 2. To find this displacement, let:

$$d_i = \begin{bmatrix} dx_i \\ dy_i \\ dz_i \end{bmatrix}, \quad (1)$$

where, $dx_i$, $dy_i$ and $dz_i$ are the components of the displacements of each point.

3. Let $(I_i, J_i)$ be the coordinates of the $i^{th}$ point in image 1.
4. Fit planes to the triplets: $(I_i, J_i, dx_i)$, $(I_i, J_i, dy_i)$ and $(I_i, J_i, dz_i)$.
5. Find the displacements of the corner points of the image 1 by using the coordinates: (0,0), (o,L−1), (M−1, L−1) and (M−1,0), where image 1 is an M×L image.
6. Find the coordinates of the corner points of image 2 by using the coordinates of the corner points of image 1 and the displacements computed in the previous step.

This method assumes that the transformation from image 1 to image 2 is an affine one. An affine transformation is a linear transformation which preserves collinearity among the data points in the data set; i.e. if two lines are parallel in image 1, they are parallel in image 2 as well. However, to preserve distances in a three-dimensional volume, a special affine transformation is preferred, a rigid body transformation. A rigid body transformation is an affine transformation which preserves distances, lengths and angles and does not substantially deform objects. Rigid body transformations are a subset of affine transformations. All rigid body transformations are affine transformations but not all affine transformations are rigid body transformations. While the disclosed embodiments are directed to linear transformations, those skilled in the art will recognize that non-linear transformations can also be used, such as cubic spline or conformal.

The above method does not enforce the rigid body criterion on the estimates and therefore, is not a rigid body transformation. A transformation which adheres to the rigid body criterion, which comprises translation and rotation of the given data set, leaves the arrangement of the given data set substantially unchanged. Distances, lengths and angles, measured in a first image between two points, will be substantially identical to the distances, lengths and angles measured in the second image between the same two points. If the rigid body criterion is not enforced, the reconstructed images resulting from the above method may suffer from geometric distortion and may be deformed and/or skewed.

The preferred embodiments described below relate to methods for estimating the three dimensional rigid body transformations between two ultrasonic data sets acquired by translating and/or rotating a transducer that may avoid deformation and/or skewing. The preferred embodiments enforce the rigid body criterion on the estimated local displacements. They employ transformation functions classified as being within the rotation group, special orthogonal group of order 3 transformations ("SO(3)"). See C. M. Brown, "Some Computational Properties of Rotation Representations," Technical Report 303, University of Rochester, Department of Computer Science, Aug. 23, 1989, further describing rotation group SO(3) transformations.

The disclosed embodiments estimate the rigid body transformation using unit quaternions (also known as Euler-Rodriquez) or orthonormal matrices (also known as Euler Angles), both of which are rotation group SO(3) transformations. It will be appreciated by one of ordinary skill in the art, that other transformations from this classification can also be used, such as Conical or Cayley-Klein transformations.

The disclosed methods are applicable to one-dimensional ("1D"), two-dimensional ("2D"), three-dimensional ("3D") and larger dimensional ultrasonic data sets acquired using single-element, 1D, 1.5D, 2D and larger dimensional transducer arrays. In addition, each data set can be acquired by a different type of transducer array. The acquired data can be B-mode, Tissue Harmonic or any other ultrasonic mode such as color Doppler velocity and energy or any combination thereof The acquired data can be motion-compensated or not. One form of motion compensation is discussed in detail in U.S. Pat. No. 5,910,114, "SYSTEM AND METHOD FOR CORRECTING THE GEOMETRY OF ULTRASONIC IMAGES ACQUIRED WITH A MOVING TRANSDUCER". Another form of motion compensation is discussed in detail in "MEDICAL DIAGNOSTIC ULTRASOUND IMAGING METHODS FOR EXTENDED FIELD OF VIEW", U.S. patent application Ser. No. 09/196,986 (filed Nov. 20, 1998) to Hossack et al., assigned to the assignee of the present invention. In addition, the misalignment between images can range from very small to very large. Further, the disclosed system and method are not limited to any one method of image data acquisition. For example, the disclosed methods work with image data obtained by manual as well as mechanical movement of the transducer. Further, the disclosed methods also work with images acquired by electronically sweeping the ultrasound beam. Herein, the phrase "coupled with" is defined to mean directly connected to or indirectly connected with through one or more intermediate components.

As can be seen from the example above, each image is formed from a data set representing multiple spatial locations. The disclosed embodiments find the rigid body transformation of these data points from one data set to another. In each data set, the data points have a particular arrangement characteristic. This arrangement characteristic is given by each data point's coordinate location in relation to all of the other data points in the data set and can be expressed as distances, lengths and angles between the data points. When computing the rigid body transformation, this arrangement characteristic is preferably preserved in the resultant transformation. That is, as the data points are translated and rotated from one image to the next, the arrangement among the individual data points of the image, relative to the other data points, remains unchanged.

II. The Preferred System

Figure 3:
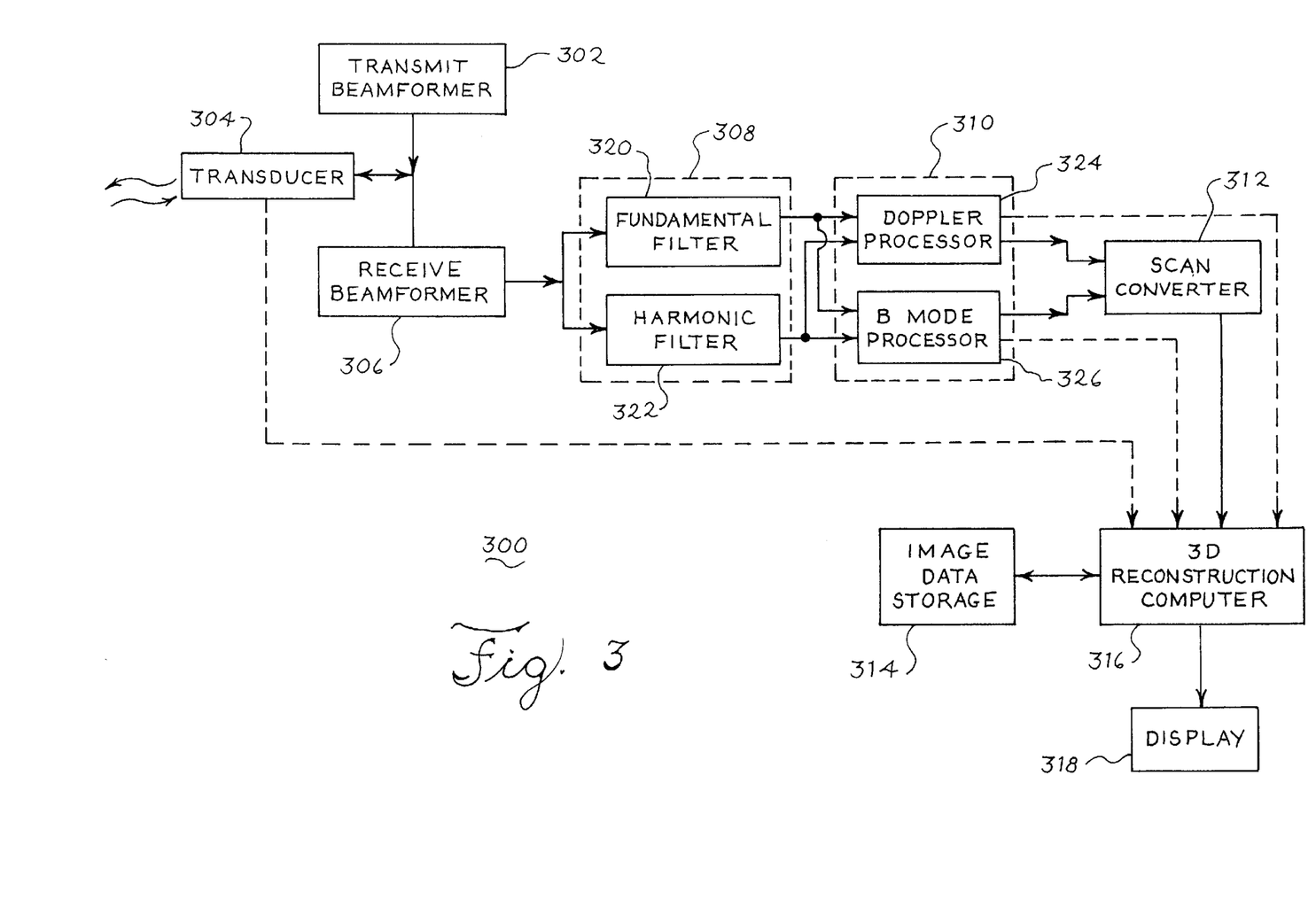
FIG. 3 depicts a block diagram of an exemplary ultrasound imaging system according to one preferred embodiment.

Referring back to the figures, and in particular, FIG. 3, an exemplary ultrasound system is generally shown at 300. The ultrasound system 300 includes a transmit beamformer 302, a transducer 304, a receive beamformer 306, a filter block 308, a signal processor 310, a scan converter 312, an image data storage 314, a three-dimensional reconstruction computer 316 and a display 318. The exemplary ultrasound system 300 is configurable to acquire information corresponding to a plurality of two-dimensional representations or image planes of a subject for three-dimensional reconstruction. Other systems, such as those for acquiring data with a two dimensional, 1.5 dimensional or single element transducer array, may be used. To generate each of the plurality of two-dimensional representations of the subject during an imaging session, the ultrasound system 300 is configured to transmit, receive and process during a plurality of transmit events. Each transmit event corresponds to firing one or more ultrasound scan lines into the subject.

The transmit beamformer 302 is of a construction known in the art, such as a digital or analog based beamformer capable of generating signals at different frequencies. The transmit beamformer 302 generates one or more excitation signals. Each excitation signal has an associated center frequency. As used herein, the center frequency represents the frequency in a band of frequencies approximately corresponding to the center of the amplitude distribution. Preferably, the center frequency of the excitation signals is within the 1 to 15 MHz range, such as 2 MHz, and accounts for the frequency response of the transducer 14. The excitation signals preferably have non-zero bandwidth.

Control signals are provided to the transmit beamformer 302 and the receive beamformer 306. The transmit beamformer 302 is caused to fire one or more acoustic lines in each transmit event, and the receive beamformer 306 is caused to generate in-phase and quadrature (I and Q) information along one or more scan lines. Alternatively, real value signals may be generated. A complete frame of information corresponding to a two-dimensional representation (a plurality of scan lines) is preferably acquired before information for the next frame is acquired.

Upon the firing of one or more ultrasound scan lines into the subject, some of the acoustical energy is reflected back to the transducer. In addition to receiving signals at the fundamental frequency (i.e., the same frequency as that transmitted), the non-linear characteristics of tissue or optional contrast agents also produce responses at harmonic frequencies. Harmonic frequencies are frequencies associated with non-linear propagation or scattering of transmit signals. As used herein, harmonic includes subharmonics and fractional harmonics as well as second, third, fourth, and other higher harmonics. Fundamental frequencies are frequencies corresponding to linear propagation and scattering of the transmit signals of the first harmonic. Non-linear propagation or scattering corresponds to shifting energy associated with a frequency or frequencies to another frequency or frequencies. The harmonic frequency band may overlap the fundamental frequency band.

The filter block 308 passes information associated with a desired frequency band, such as the fundamental band using fundamental band filter 320 or a harmonic frequency band using the harmonic band filter 322. The filter block 308 may be included as part of the receive beamformer 306. Furthermore, the fundamental band filter 320 and the harmonic band filter 322 preferably comprise one filter that is programmable to pass different frequency bands, such as the fundamental, second or third harmonic bands. For example, the filter block 308 demodulates the summed signals to baseband. The demodulation frequency is selected in response to the fundamental center frequency or another frequency, such as a second harmonic center frequency. For example, the transmitted ultrasonic waveforms are transmitted at a 2 MHz center frequency. The summed signals are then demodulated by shifting by either the fundamental 2 MHz or the second harmonic 4 MHz center frequencies to baseband (the demodulation frequency). Other center frequencies may be used. Signals associated with frequencies other than near baseband are removed by low pass filtering. As an alternative or in addition to demodulation, the filter block 308 provides band pass filtering. The signals are demodulated to an intermediate frequency (IF)(e.g. 2 MHz) or not demodulated and a band pass filter is used. Thus, signals associated with frequencies other than a range of frequencies centered around the desired frequency or an intermediate frequency (IF) are filtered from the summed signals. The demodulated or filtered signal is passed to the signal processor 310 as the complex I and Q signal, but other types of signals, such as real value signals, may be passed.

By selectively filtering which frequencies are received and processed, the ultrasound system 300 produces images with varying characteristics. In tissue harmonic imaging, no additional contrast agent is added to the target, and only the nonlinear characteristics of the tissue are relied on to create the ultrasonic image. Medical ultrasound imaging is typically conducted in a discrete imaging session for a given subject at a given time. For example, an imaging session can be limited to an ultrasound patient examination of a specific tissue of interest over a period of ¼ to 1 hour, though other durations are possible. In this case, no contrast agent is introduced into the tissue at any time during the imaging session.

Tissue harmonic images provide a particularly high spatial resolution and often possess improved contrast resolution characteristics. In particular, there is often less clutter in the near field. Additionally, because the transmit beam is generated using the fundamental frequency, the transmit beam profile is less distorted by a specific level of tissue-related phase aberration than a profile of a transmit beam formed using signals transmitted directly at the second harmonic.

The harmonic imaging technique described above can be used for both tissue and contrast agent harmonic imaging. In contrast agent harmonic imaging, any one of a number of well known nonlinear ultrasound contrast agents, such as micro-spheres or the FS069 agent by Schering of Germany, are added to the target or subject in order to enhance the non-linear response of the tissue or fluid. The contrast agents radiate ultrasonic energy at harmonics of an insonifying energy at fundamental frequencies.

The signal processor 310 comprises one or more processors for generating two-dimensional Doppler or B-mode information. For example, a B-mode image, a color Doppler velocity image (CDV), a color Doppler energy image (CDE), a Doppler Tissue image (DTI), a Color Doppler Variance image, or combinations thereof may be selected by a user. The signal processor 310 detects the appropriate information for the selected image. Preferably, the signal processor 310 comprises a Doppler processor 324 and a B-mode processor 326. Each of these processors is preferably a digital signal processor and operates as known in the art to detect information. As known in the art, the Doppler processor 324 estimates velocity, variance of velocity and energy from the I and Q signals. As known in the art, the B-mode processor 326 generates information representing the intensity of the echo signal associated with the I and Q signals.

The information generated by the signal processor 310 is provided to the scan converter 312. Alternatively, the scan converter 312 includes detection steps as known in the art and described in U.S. application Ser. No. 08/806,922 (Atty. Ref. No. 5050/189), assigned to the assignee of the present invention. The scan converter 312 is of a construction known in the art for arranging the output of the signal processor 310 into two-dimensional representations or frames of image data. Preferably, the scan converter 312 outputs formatted video image data frames, using a format such as the DICOM Medical industry image standard format or a TIFF format. Thus, the plurality of two-dimensional representations are generated. Each of the representations corresponds to a receive center frequency, such as a second harmonic center frequency, a type of imaging, such as B-mode, and positional information. The harmonic based representations may have better resolution and less clutter than fundamental images. By suppressing the harmonic content of the excitation signal, the benefits of harmonic imaging of tissue may be increased.

The plurality of two-dimensional representations of the subject are stored in the image data storage 314. From here, the 3D reconstruction computer 316 operates on the stored plurality of two-dimensional representations and assembles them into a three-dimensional representation. Alternatively, the 3D computer 316 may also input pre-scan converted acoustic data to convert to 3D data sets as well. Alternatively, the 3D reconstruction computer 316 receives the 2D representations in real time and assembles the 3D reconstruction. The completed 3D reconstruction is then displayed on the display 318.

Figure 4:
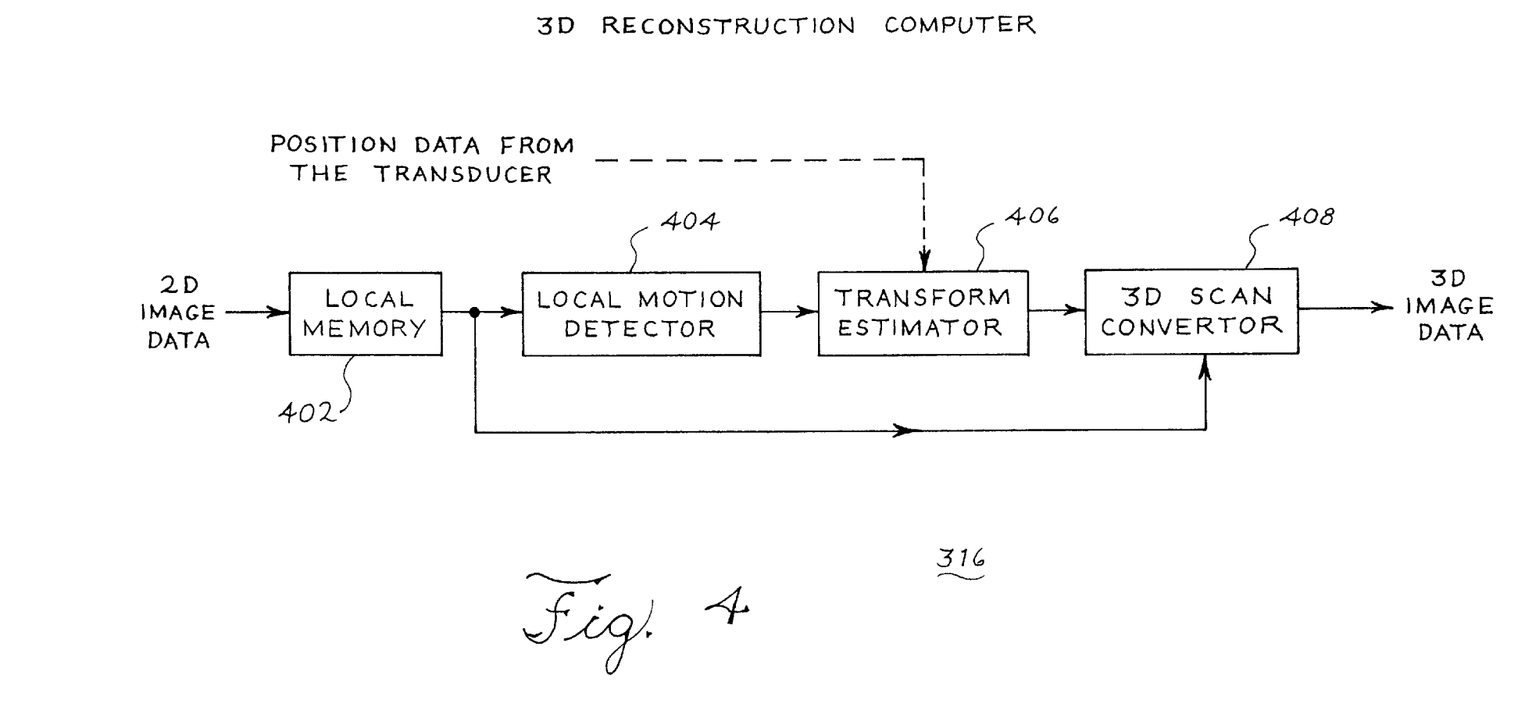
FIG. 4 depicts a block diagram of an exemplary three dimensional reconstruction computer.

Referring now to FIG. 4, there is shown a block diagram of an exemplary 3D reconstruction computer 316. The 3D reconstruction computer 316 includes a local memory 402, a local motion detector 404, a transform estimator 406 and a three-dimensional scan converter 408. The local memory 402 receives and stores the 2D representations for 3D reconstruction. Alternatively, the local memory 402 receives and stores 3D representations. The local motion detector 404 operates on two successive images at a time. The local motion detector 404 first selects a series of points (e.g. 20) in the first image. These points could be on a rectangular grid and uniformly distributed substantially over the entire image. Alternatively, they could be points corresponding to features in the first image. The features could be selected using a number of criteria such as image intensity, maximum local image gradient, entropy or texture content. Following this for each selected point in image 1, local motion is estimated using the speckle correlation technique as is known in the art. In this technique, for each point for which the local motion is computed, a neighborhood of points in the first image is cross-correlated with a similar neighborhood of points in the second image. This technique is similar to the technology frequently used in MPEG motion picture compression standard. Other methods such as feature correlation, speckle decorrelation, time delays, spectral broadening, power and spectral peak may also be used for local motion detection. The transform estimator 406 receives the local motion estimates from the local motion detector 404. Using the local motion estimates for the selected set of points in the first image, it then computes the coordinates of the corresponding set of points in the second image. Alternatively, the transform estimator 406 directly receives the coordinates of the selected set of points in the first image and the corresponding set of points in the second image directly from the transducer, which contains a position sensing device such as a magnetic position sensor, optical position sensor, mechanical position sensor, an acoustic position sensor or other sensor or sensors as is known in the art. The transform estimator 406 then computes the rigid body transformation using unit quaternions or orthonormal matrices as disclosed by the methods described below. This rigid body transformation is preferably computed so as to minimize the error between points, such as by using a least squares algorithm (minimize the sum of the squared differences) or, alternatively, a weighted least squares algorithm.

The 3D Scan Converter 408 receives the rigid body transformation data for each successive pair of images from the transform estimator 406 and the image data from the local memory 402. It then generates a 3D grid data set corresponding to the scanned object and outputs this to the display 318.

III. First Rigid Body Criterion Embodiment

The first preferred embodiment for computing the rigid body transformation represents data points and transformations as quatemions. Quatemions are four dimensional vectors used to represent rigid body transformations. Referring to FIG. 2 which shows exemplary image planes 1 and 2, points $p_i$, (i=0 ... N−1), in image 1 are estimated to be displaced to points $q_i$, (i=0 ... N−1), in image 2 using the above described techniques for estimating local displacement. The points for which the local displacements are calculated are selected by using a predefined criteria such as points spaced equally along the range direction, points with highest image information content or points placed by the user. Let us define $p_i$ and $q_i$ as quaternions:

$$p_i = (0 + ix_{p,i} + jy_{p,i} + kz_{p,i}), \qquad (2)$$

$$q_i = (0 + ix_{q,i} + jy_{q,i} + kz_{q,i}), \qquad (3)$$

where, $X_{p,i}$, $y_{p,i}$ and $z_{p,i}$ are the coordinates of the point $p_i$. Similarly $x_{q,i}$, $Y_{q,i}$ and $z_{q,i}$ are the coordinates of the point $q_i$. Let the unit quaternion, r, describe the rotation between the two coordinate spaces and the quaternion, t, describe the translation. Defining the rigid body transformation between the two spaces as: T=(r,t), then:

$$q_i = rp_i r^* + t + \epsilon_i, \qquad (4)$$

where, $\epsilon_i$, is the error between the predicted and actual $i^{th}$ point in image 2 and r * is the conjugate of r. The error parameter $\chi^2$ for all points is defined as follows:

$$\chi^2 = \sum_{i=0}^{N-1} \frac{\epsilon_i^2}{\sigma_i^2} \qquad (5)$$

$$= \sum_{i=0}^{N-1} \frac{1}{\sigma_i^2} |q_i - rp_i r^* - t|^2, \qquad (6)$$

where, $\sigma_i$ is the standard deviation of error between the predicted and actual $i^{th}$ point in image 2. $\sigma_i$ may denote the confidence of the $i^{th}$ point being accurate. If the $i^{th}$ point is highly accurate, $\sigma_i$ is either estimated or selected to be low. If the ith point is not very accurate, $\sigma_i$ is large.

The transformation, T, that minimizes the sum of the squared error, $\chi^2$, is found using the following steps:

1. First, the centers of gravity, $c_p$ and $c_q$ of the sets of points in each space are found according to the following equations:

$$C_p = \frac{\sum_{i=0}^{N-1} \frac{p_i}{\sigma_i^2}}{\sum_{i=0}^{N-1} \frac{1}{\sigma_i^2}} \qquad (7)$$

$$c_q = \frac{\sum_{i=0}^{N-1} \frac{q_i}{\sigma_i^2}}{\sum_{i=0}^{N-1} \frac{1}{\sigma_i^2}} \qquad (8)$$

2. New coordinate systems in each space centered around $c_p$ and $c_q$ are next defined by the following equations:

$$\hat{p}_i = p_i - c_p \qquad (9)$$

$$\hat{q}_i = q_i - c_q. \qquad (10)$$

In these new coordinate systems, the translation that minimizes $\chi^2$ is the null quaternion. Utilizing the null quaternion, then, Equation 4 reduces to:

$$\hat{q}_i = r\hat{p}_i r^* + \epsilon_i, \qquad (11)$$

Note that the rotation is now decoupled from the translation. The rotation is then estimated as follows.

3. The rotation that minimizes $\chi^2$ is then obtained by forming the matrix:

$$N = \begin{bmatrix} N_{11} & N_{12} & N_{13} & N_{14} \\ N_{21} & N_{22} & N_{23} & N_{24} \\ N_{31} & N_{32} & N_{33} & N_{34} \\ N_{41} & N_{42} & N_{43} & N_{44} \end{bmatrix}, \qquad (12)$$

where, $$N_{11} = S_{xx} + S_{yy} + S_{zz} \qquad (13)$$

$$N_{12} = S_{yz} - S_{zy} \qquad (14)$$

$$N_{13} = S_{zx} - S_{xz} \qquad (15)$$

$$N_{14} = S_{xy} - S_{yx} \qquad (16)$$

$$N_{21} = S_{yz} - S_{zy} \qquad (17)$$

$$N_{22} = S_{xx} - S_{yy} - S_{zz} \qquad (18)$$

$$N_{23} = S_{xy} + S_{yx} \qquad (19)$$

$$N_{24} = S_{zx} + S_{xz} \qquad (20)$$

$$N_{31} = S_{zx} - S_{xz} \qquad (21)$$

$$N_{32} = S_{xy} + S_{yx} \qquad (22)$$

$$N_{33} = S_{xx} + S_{yy} - S_{zz} \qquad (23)$$

$$N_{34} = S_{yz} + S_{zy} \qquad (24)$$

$$N_{41} = S_{xy} - S_{yx} \qquad (25)$$

$$N_{42} = S_{zx} + S_{xz} \qquad (26)$$

$$N_{43} = S_{yz} + S_{zy} \qquad (27)$$

$$N_{44} = -S_{xx} - S_{yy} + S_{zz}, \qquad (28)$$

and:

$$S_{xx} = \sum_{i=0}^{N-1} \frac{\hat{x}_{p,i} \hat{x}_{q,i}}{\sigma_i^2} \qquad (29)$$

$$S_{xy} = \sum_{i=0}^{N-1} \frac{\hat{x}_{p,i} \hat{y}_{q,i}}{\sigma_i^2} \qquad (30)$$

$$S_{xz} = \sum_{i=0}^{N-1} \frac{\hat{x}_{p,i} \hat{z}_{q,i}}{\sigma_i^2} \qquad (31)$$

$$S_{yx} = \sum_{i=0}^{N-1} \frac{\hat{y}_{p,i} \hat{x}_{q,i}}{\sigma_i^2} \qquad (32)$$

$$S_{yy} = \sum_{i=0}^{N-1} \frac{\hat{y}_{p,i} \hat{y}_{q,i}}{\sigma_i^2} \qquad (33)$$

$$S_{yz} = \sum_{i=0}^{N-1} \frac{\hat{y}_{p,i} \hat{z}_{q,i}}{\sigma_i^2} \qquad (34)$$

-continued $$S_{zx} = \sum_{i=0}^{N-1} \frac{\hat{z}_{p,i}\hat{x}_{q,i}}{\sigma_i^2} \quad (35)$$

$$S_{zy} = \sum_{i=0}^{N-1} \frac{\hat{z}_{p,i}\hat{y}_{q,i}}{\sigma_i^2} \quad (36)$$

$$S_{zz} = \sum_{i=0}^{N-1} \frac{\hat{z}_{p,i}\hat{z}_{q,i}}{\sigma_i^2} \quad (37)$$

4. The rotation quaternion, r, is given by the unit eigen vector corresponding to the most positive eigen value of the matrix N. When one or more sets of points lie on a plane, as is the case with the data set acquisition methods known in the art, a closed form solution for the rotation, r, exists and is presented in B. K. P. Horn, "Closed-Form Solution of Absolute Orientation Using Unit Quaternions," *Journal of Optical Society of America A*, vol. 4, pp. 629–42, April 1987. Alternatively, other solutions for the rotation, r, known to those skilled in that art, can also be used. The computer program contained in the attached appendix (discussed in more detail below) utilizes this closed form solution.

Note that the translation is implicit in equations 7 and 8. After equations 9 and 10 are defined in the new coordinate system, the translation is zero.

Once $c_p$, $c_q$ and r are found, any point $p_o$ in the image 1 can be transformed into its corresponding point $q_o$ in image 2 as follows:

Step 1-compute $\hat{p}_o = p_o - c_p$ (38)

Step 2-compute $\hat{q}_o = r\hat{p}_o r^*$ (39)

Step 3-compute $q_o = \hat{q}_o + c_q$ (40)

Note that because a closed form solution exists for the rotation quaternion r, the computation of the above transformation can be executed very quickly by a digital computer. This represents a significant advantage over other methods of computing rigid body transformations wherein these other methods are much more computationally intensive because closed form solutions do not exist for them.

Figure 5:
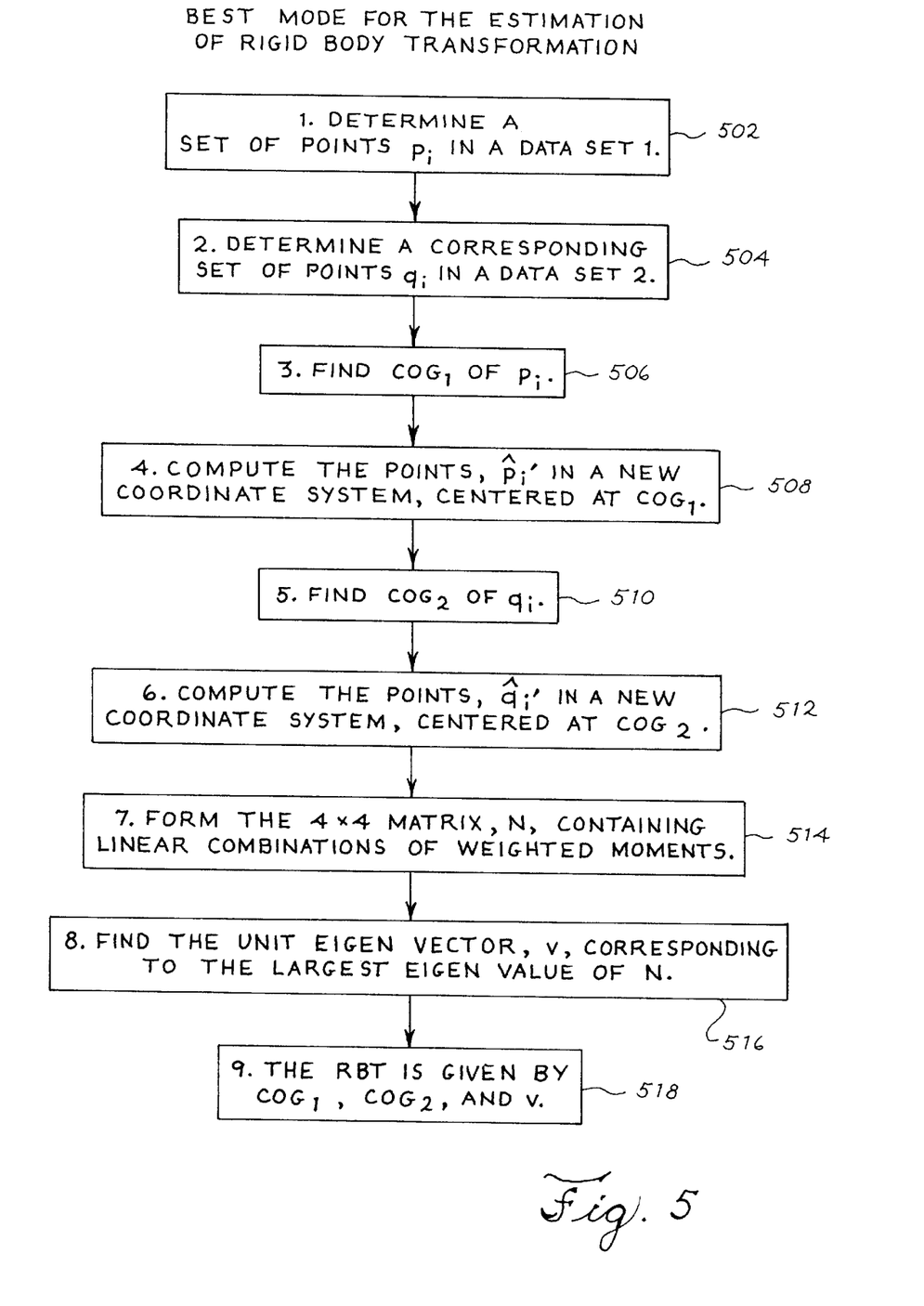
FIG. 5 shows a flow chart for estimating a three dimensional rigid body transformation according to a first preferred method.

Referring now to FIG. 5, there is shown a flow chart for an exemplary computer program to compute the rigid body transformation using quaternions. The program operates on two data sets representing two ultrasonic images. First, a set of points, $p_i$, is determined in the first data set (Block 502). A corresponding set of points, $q_i$, is determined in a second data set (Block 504). The points for which the local displacements are calculated are selected by using a predefined criteria such as points spaced equally along the range direction, points with highest image information content or points placed by the user. Next, a first center of gravity ("COG") is computed for the first set of data points, $p_i$ (Block 506). Once the first COG is computed, a new set of data points, $\hat{p}_i$, is computed in a new coordinate system centered about this first COG (Block 508). A second COG is then computed for the second set of data point $q_i$, (Block 510) and a new set of data points, $\hat{q}_i$, is computed in a new coordinate system centered about this second COG (Block 512). A 4×4 matrix containing linear combinations of weighted moments, N, is then formed using equations 12–37 above (Block 514). Next, the unit eigen vector, v, corresponding to the largest eigen value of the matrix, N, is found (Block 516). Finally, the rigid body transformation is given by the first COG (Block 506), the second COG (Block 510) and the unit eigen vector, v, (Block 516) using equations 38–40 (Block 518).

The source code of an exemplary computer program which performs the above algorithm is attached herein as a microfiche appendix. This program can be compiled using the gnu c++ compiler, published by The Free Software Foundation, located in Boston, Mass., the Visual C++ compiler, published by Microsoft Corporation, located in Redmond, Washington, or any other C++ compiler. It runs under Sun OS, published by Sun Microsystems, Inc., located in Mountain View, Calif., Linux, published by Red hat, located in Durham, N.C. and Windows NT, published by Microsoft Corporation located in Redmond, Wash.

The main function, "find_weighted_transformation" accepts 4 parameters: (1) a set of points in the first image, (2) a set of points in the second image, (3) a set of sigma's corresponding to weights and (4) the number of points. It gets these parameters from the module where the points are selected as described elsewhere in the specification. This function outputs a record structure called "transform" which contains the two center of gravity's and the rotation quaternion.

IV. Second Rigid Body Criterion Embodiment

The second preferred embodiment for computing the rigid body transformation utilizes orthonormal matrices to represent data points and transformations. An orthonormal matrix is defined as a matrix, that when multiplied by its own transpose, yields the identity matrix. The points for which the local displacements are calculated are selected by using a predefined criteria such as points spaced equally along the range direction, points with highest image information content or points placed by the user. Again referring to FIG. 2 which shows exemplary image planes 1 and 2, points $p_i$, (i=0 . . . N–1), in image 1 are estimated to be displaced to points $q_i$, (i=0 . . . N–1), in image 2. This method begins by defining $p_i$ and $q_i$ as vectors:

$$p_i = \begin{bmatrix} x_{p,i} \\ y_{p,i} \\ z_{p,i} \end{bmatrix} \quad (41)$$

$$q_i = \begin{bmatrix} x_{q,i} \\ y_{q,i} \\ z_{q,i} \end{bmatrix} \quad (42)$$

The orthonormal matrix, R, describes the rotation between the two coordinate spaces and vector, t, describes the translation. The rigid body transformation between the two spaces is defined to be: T=(R,t). Then:

$$q_i = Rp_i + t + \epsilon_i, \quad (43)$$

where, $\epsilon_i$, is, as before, the error between the predicted and actual $i^{th}$ point in image 2. The error parameter $\chi^2$ for all points is defined as follows:

$$\chi^2 = \sum_{i=0}^{N-1} \frac{\epsilon_i^2}{\sigma_i^2} \quad (44)$$

$$= \sum_{i=0}^{N-1} \frac{1}{\sigma_i^2} |q_i - Rp_i - t|^2, \quad (45)$$

where, $\sigma_i$ is the standard deviation of error between the predicted and actual $i^{th}$ point in image 2. $\sigma_i$ may denote the confidence of the $i^{th}$ point being accurate. If the $i^{th}$ point is highly accurate, $\sigma_i$ is either estimated or selected to be low. If the $i^{th}$ point is not very accurate, $\sigma_i$ is large.

The transformation, T, that minimizes the sum of squared error, $\chi^2$, is found by the following method:

1. First, find the centers of gravity, $c_p$ and $c_q$, of the sets of points in each space:

$$C_p = \frac{\sum_{i=0}^{N-1} \frac{p_i}{\sigma_i^2}}{\sum_{i=0}^{N-1} \frac{1}{\sigma_i^2}} \quad (46)$$

$$c_q = \frac{\sum_{i=0}^{N-1} \frac{q_i}{\sigma_i^2}}{\sum_{i=0}^{N-1} \frac{1}{\sigma_i^2}} \quad (47)$$

2. Next, define new coordinate systems in each space centered around $c_p$ and $c_q$, respectively;

$$\hat{p}_i = p_i - c_p \quad (48)$$

$$\hat{q}_i = q_i - c_q. \quad (49)$$

In these new coordinate systems, the translation that minimizes $\chi^2$ is the null vector. Utilizing the null vector, equation 43 reduces to:

$$\hat{q}_i = R\hat{p}_i + \epsilon_i, \quad (50)$$

This decouples rotation from translation. Note that the translation is implicit in equations 46 and 47. After equations 48 and 49 are defined in the new coordinate system, the translation is zero. The next step is to find the rotation matrix, R, that minimizes $\chi^2$. Let:

$$M = \begin{bmatrix} S_{xx} & S_{xy} & S_{xz} \\ S_{yx} & S_{yy} & S_{yz} \\ S_{zx} & S_{zy} & S_{zz} \end{bmatrix} \quad (51)$$

The rotation matrix, R, is then found in one of two ways:

(a) by using singular value decomposition of M. This technique is described in K. S. Arun, T. S. Huang, and S. D. Blostein, "Least-Squares Fitting of Two 3D Point Sets," IEEE Transactions on Pattern Analysis and Machine Intelligence, vol. PAMI-9, no. 5, pp. 698–700, 1987. Alternatively, other techniques of singular value decomposition, known to those skilled in the art, can also be used.

(b) by using eigen value decomposition of $M^T M$. This technique is described in B. K. P. Horn, H. M. Hilden, and S. Negahdaripour, "Closed-Form Solution of Absolute Orientation Using Orthonormal Matrices," Journal of Optical Society of America A, vol. 5, pp. 1127–35, July 1988. Alternatively, other techniques for eigen value decomposition, known to those skilled in the art, can also be used.

A. Singular Value Decomposition

The matrix M is first decomposed into its singular values. Utilizing matrix M from equation 51, let:

$$M = U\Sigma V^T, \quad (52)$$

where, U and V are orthonormal matrices and $$\sum = \begin{bmatrix} \delta_1 & 0 & 0 \\ 0 & \delta_2 & 0 \\ 0 & 0 & \delta_3 \end{bmatrix}, \quad (53)$$

with $\delta_i$ being the singular values. Then the rotation matrix, R, is given by:

$$R = VU^T \quad (54)$$

B. Eigen Value Decomposition

Utilizing eigen value decomposition, the eigen values of the matrix $M^T M$, $\lambda_1$, $\lambda_2$, and $\lambda_3$, and the corresponding unit eigen vectors, $u_1$, $u_2$ and $u_3$ are found by methods known in the art as disclosed above. Once these values are found, then find:

$$(M^T M)^{-\frac{1}{2}} = \frac{1}{\sqrt{\lambda_1}} u_1 u_1^T + \frac{1}{\sqrt{\lambda_2}} u_2 u_2^T + \frac{1}{\sqrt{\lambda_3}} u_3 u_3^T \quad (55)$$

Then the rotation matrix, R, is given by:

$$R = M(M^T M)^{-\frac{1}{2}} \quad (56)$$

Once $c_p$, $c_q$ and R are found, any point $p_o$ in the image 1 can be transformed into its corresponding point $q_o$ in image 2 as follows:

Step 1-compute $\hat{p}_o = p_o - c_p$ (57)

Step 2-compute $\hat{q}_o = R\hat{p}_o$ (58)

Step 3-compute $q_o = \hat{q}_o + c_q$ (59)

Figure 6:
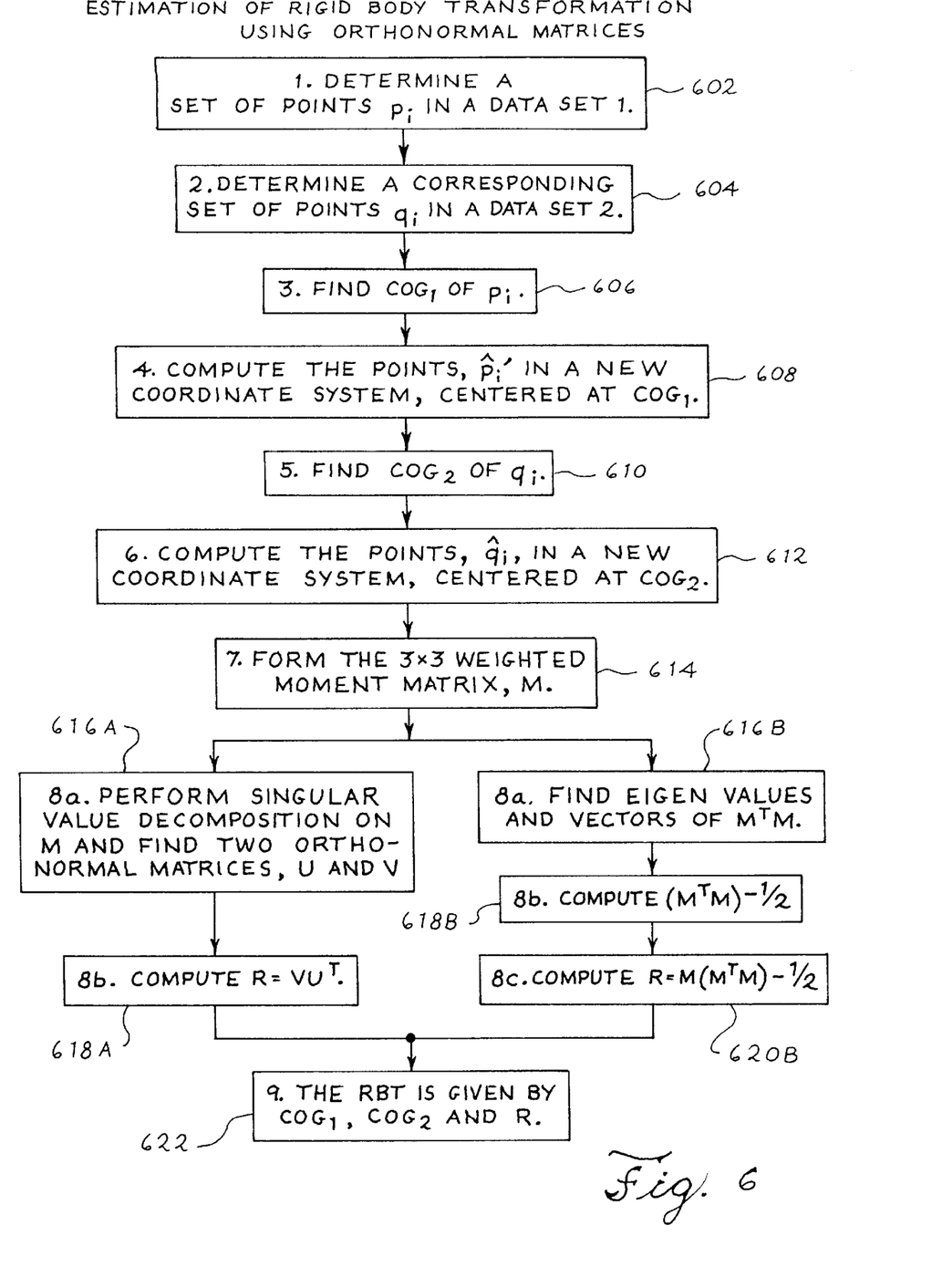
FIG. 6 shows a flow chart for estimating a three dimensional rigid body transformation according to a second preferred method.

Referring now to FIG. 6, there is shown a flow chart for an exemplary computer program to compute the rigid body transformation using orthonormal matrices. The program operates on two data sets representing two ultrasonic images. First, a set of points, $p_i$, is determined in the first data set (Block 602). A corresponding set of points, $q_i$, is determined in a second data set (Block 604). The points for which the local displacements are calculated are selected by using a predefined criteria such as points spaced equally along the range direction, points with highest image information content or points placed by the user. Next, a first center of gravity ("COG") is computed for the first set of data points, $p_i$ (Block 606). Once the first COG is computed, a new set of data points, $\hat{p}_i$, is computed in a new coordinate system centered about this first COG (Block 608). A second COG is then computed for the second set of data point $q_i$, (Block 610) and a new set of data points, $\hat{q}_i$, is computed in a new coordinate system centered about this second COG (Block 612). A 3×3 weighted moment matrix, M, is then formed using equation 51 and corresponding equations from equations 29–37 above (Block 614).

Next, a singular value decomposition is performed on M and the two orthonormal matrices, U and V are found (Block 616A). The rotation matrix is then computed by $R = VU^T$ (Block 618A).

Alternatively, the eigen values and eigen vectors of $M^T M$ can be found (Block 616B). The matrix $(M^T M)^{-\frac{1}{2}}$ is then computed (Block 618B). Then the rotation matrix is computed as $R = M(M^T M)^{-\frac{1}{2}}$ (Block 620B).

Finally, the rigid body transformation is given by the first COG (Block 606), the second COG (Block 610) and the rotation matrix, R, using equations 57–59 (Block 622).

In an alternative embodiment, the estimation of rigid body transformation between two ultrasonic data sets can be applied to the situation where as the two data sets are acquired, the object may change shape due to transducer pressure, patient motion or other factors. In this situation, a global rigid body transformation for the entire data set may not be applicable. Therefore, multiple rigid body transformations can be applied in respective small regions in the data set. Using this embodiment, a multitude of local rigid body transformations describing local regions of the data set are computed using the disclosed techniques on subsets of the larger ultrasonic data set. These sub-regions may be selected using image segmentation methods based on optical flow, texture, connectivity or border detection. Alternatively the user may select them manually as well.

In another alternative embodiment, the unit quaternion, r, in equation 4 and the orthonormal matrix, R, in equation 43 may be replaced with a non-unit quaternion, $\bar{r}$, and a non-orthonormal matrix, $\bar{R}$. This is useful in order to model more complex object deformations that can occur between the two data sets.

It is to be understood that a wide range of changes and modifications to the embodiments described above will be apparent to those skilled in the art, and are contemplated. For example, larger or smaller matrices can be used in the transformation computations or alternate mathematical equations could be used. Furthermore, the transformation which maps the first image to the second can be an almost rigid body transformation wherein the objects in the images may change shape within pre-defined bounds or limits. Alternatively, some parts of the first image can be subject to a rigid body transformation while other parts are subject to a more general linear or non-linear transformation. Further, the disclosed methods can be executed on a variety of hardware, including digital and analog processors and can be executed in real time or on stored data. In addition, it will be appreciated that the rigid body transformation computations on the ultrasound data can be performed remotely from the ultrasound system, such as on a remote 3D reconstruction computer.

It is therefore intended that the foregoing detailed description be regarded as illustrative rather than limiting, and that it be understood that it is the following claims, including all equivalents, that are intended to define the spirit and scope of this invention.

What is claimed is:

1. In a medical diagnostic ultrasound system which acquires a plurality of ultrasonic data sets of a human or animal, a method for estimating a transformation between: a first data set of said plurality of ultrasonic data sets, said first data set comprising a first plurality of data points, said first plurality of data points having a first arrangement characteristic in a first coordinate system, said first arrangement characteristic comprising distances, lengths and angles between two or more of said first plurality of data points; and a second data set of said plurality of ultrasonic data sets, said second data set comprising a second plurality of data points, said second plurality of data points having a second arrangement characteristic in a second coordinate system, said second arrangement characteristic comprising distances, lengths and angles between two or more of said second plurality of data points, said method comprising:

(a) calculating a transformation between said first and second data sets wherein said transformation is a rotation group, special orthogonal group of order 3 transformation selected from the group consisting of quaternion and orthonormal matrix;

(b) preserving said first arrangement characteristic in said second coordinate system using said transformation; and (c) approximating said second arrangement characteristic using said transformation.

2. The method of claim 1, wherein (a) further comprises calculating rotation and translation.

3. The method of claim 2, further comprising:

(b) finding a first center of gravity in said first data set wherein said first coordinate system is centered about said first center of gravity; and (c) finding a second center of gravity in said second data set wherein said second coordinate system is centered about said second center of gravity.

4. The method of claim 3, wherein said translation is calculated from said first and second centers of gravity.

5. The method of claim 2, wherein said calculation of rotation further comprises:

(d) computing a matrix; and (e) finding the quaternion given by the eigen vector corresponding to the most positive eigen value of said matrix.

6. The method of claim 5, wherein said matrix is a matrix containing linear combinations of weighted moments.

7. The method of claim 5, wherein said matrix is a matrix containing linear combinations of un-weighted moments.

8. The method of claim 5, wherein said matrix is the 4×4 weighted moment matrix N where:

$$N = \begin{bmatrix} N_{11} & N_{12} & N_{13} & N_{14} \\ N_{21} & N_{22} & N_{23} & N_{24} \\ N_{31} & N_{32} & N_{33} & N_{34} \\ N_{41} & N_{42} & N_{43} & N_{44} \end{bmatrix}.$$

9. The method of claim 2, wherein said calculation of rotation further comprises:

(d) computing a matrix;

(e) performing singular value decomposition of said matrix into first and second orthonormal matrices; and (f) computing a matrix product of said first and second orthonormal matrices.

10. The method of claim 9, wherein said matrix is a matrix containing linear combinations of weighted moments.

11. The method of claim 9, wherein said matrix is a matrix containing linear combinations of un-weighted moments.

12. The method of claim 9, wherein said matrix is the matrix M given by:

$$M = \begin{bmatrix} S_{xx} & S_{xy} & S_{xz} \\ S_{yx} & S_{yy} & S_{yz} \\ S_{zx} & S_{zy} & S_{zz} \end{bmatrix}.$$

13. The method of claim 2, wherein said calculation of rotation further comprises:

(d) computing a matrix;

(e) computing a second matrix by multiplying said matrix by the transpose of said matrix;

(f) performing eigen value decomposition of said second matrix;

(g) computing a third matrix as the inverse square root of said second matrix using said eigen value decomposition; and (h) computing a matrix product of said first and third matrices.

14. The method of claim 13, wherein said matrix is a matrix containing linear combinations of weighted moments.

15. The method of claim 13, wherein said matrix is a matrix containing linear combinations of un-weighted moments.

16. The method of claim 13, wherein said second matrix is the matrix $M^T M$ where M is said first matrix and:

$$M = \begin{bmatrix} S_{xx} & S_{xy} & S_{xz} \\ S_{yx} & S_{yy} & S_{yz} \\ S_{zx} & S_{zy} & S_{zz} \end{bmatrix}.$$

17. The method of claim 16, wherein said third matrix is given by $(M^T M)^{-\frac{1}{2}}$ and said matrix product is given by $M(M^T M)^{-\frac{1}{2}}$.

18. The method of claim 1, wherein in (a) comprises calculating unit quaternions.

19. The method of claim 1, wherein in (a) comprises calculating orthonormal matrices.

20. The method of claim 1, further comprising:
(b) minimizing the sum of the squared error of said transformation.

21. The method of claim 1, further comprising:
(b) minimizing the sum of the weighted squared error of said transformation.

22. The method of claim 1, wherein (a) comprises calculating between first and second data subsets of one or more larger ultrasonic data sets.

23. The method of claim 1, wherein (a) comprises calculating between first and second data sets representing a two dimensional ultrasonic image plane.

24. The method of claim 1, wherein (a) comprises calculating between first and second data sets representing portions of a two dimensional ultrasonic image plane.

25. The method of claim 1, wherein (a) comprises calculating between first and second data sets representing a three dimensional ultrasonic image volume.

26. The method of claim 1, wherein (a) comprises calculating between first and second data sets representing portions of a three dimensional ultrasonic image volume.

27. The method of claim 1, wherein (a) comprises calculating a rigid body transformation.

28. An ultrasound system for medical imaging or therapy comprising:
a memory operative to store first and second ultrasonic data sets, each of which comprises a plurality of ultrasonic data, each of said data sets having an arrangement characteristic among each of said plurality of ultrasonic data, said arrangement characteristic comprising distances, lengths and angles between two or more of said plurality of ultrasonic data;
a processor coupled with said memory and operative to receive said data sets from said memory and compute a transformation from said first data set to said second data set which preserves said arrangement characteristic of said first data set while approximating said arrangement characteristic of said first data set to said arrangement characteristic of said second data set, wherein said transformation is a rotation group, special orthogonal group of order 3 transformation selected from the group consisting of quaternion and orthonormal matrix.

29. The ultrasound system of claim 28, wherein said processor is operative to compute rotation and translation from said ultrasonic data.

30. The ultrasound system of claim 29, wherein said processor is operable to compute said rotation from a matrix and the eigen vector corresponding to the most positive eigen value of said matrix.

31. The ultrasound system of claim 29, wherein said processor is operable to compute said rotation from a matrix and a matrix-product, said matrix-product computed from first and second orthonormal matrices.

32. The ultrasound system of claim 31, wherein said first and second orthonormal matrices are computed from the singular value decomposition of said matrix.

33. The ultrasound system of claim 31, wherein said matrix product is given by multiplying said first orthonormal matrix by the transpose of said second orthonormal matrix.

34. The ultrasound system of claim 29, wherein said processor is operable to compute said rotation from a matrix-product of a matrix and the inverse square root of an eigen value decomposition of the product of said matrix and the transpose of said matrix.

35. The ultrasound system of claim 28, wherein said processor is operative to compute said transformation using quaternions.

36. The ultrasound system of claim 28, wherein said processor is operative to compute said transformation using orthonormal matrices.

37. The ultrasound system of claim 28, wherein said processor is operative to estimate said transformation with a minimized squared error sum.

38. The ultrasound system of claim 28, wherein said processor is operative to estimate said transformation with a minimized weighted squared error sum.

39. The ultrasound system of claim 28, wherein said first and second ultrasonic data sets represent subsets of one or more larger ultrasonic data sets.

40. The ultrasound system of claim 28, wherein said first and second ultrasonic data sets represent a two dimensional ultrasonic image plane.

41. The ultrasound system of claim 28, wherein said first and second ultrasonic data sets represent portions of a two dimensional ultrasonic image plane.

42. The ultrasound system of claim 28, wherein said first and second ultrasonic data sets represent a three dimensional ultrasonic image volume.

43. The ultrasound system of claim 28, wherein said first and second ultrasonic data sets represent portions of a three dimensional ultrasonic image volume.

44. The ultrasound system of claim 28, wherein said transformation comprises a rigid body transformation.

45. An ultrasound system for medical imaging or therapy comprising:
means to store ultrasonic data into first and second data sets, each of said one or more data sets having an arrangement characteristic, said arrangement characteristic comprising distances, lengths and angles between two or more of said ultrasonic data;
means to process said first and second data sets from said means to store and compute a transformation from said first data set to said second data set which preserves said arrangement characteristic of said first data set while approximating said arrangement characteristic of said second data set, wherein said transformation is a rotation group, special orthogonal group of order 3 transformation selected from the group consisting of quaternion and orthonormal matrix.

46. The ultrasound system of claim 45, wherein said transformation comprises a rigid body transformation.

47. The ultrasound system of claim 45, wherein said processing means further comprises means to compute quaternions from said first and second data sets.

48. The ultrasound system of claim 45, wherein said processing means further comprises means to compute orthonormal matrices from said first and second data sets.

49. The ultrasound system of claim 45, wherein said processing means further comprises means to compute rotation and translation.

50. The ultrasound system of claim 45, wherein said processing means is further operative to minimize the least squared error between said first and said second data sets for said computed transformation.

51. The ultrasound system of claim 45, wherein said processing means is further operative to minimize the weighted least squared error between said first and said second data sets for said computed transformation.

52. The ultrasound system of claim 45, wherein said first and second data sets represent subsets of one or more larger ultrasonic data sets.

53. The ultrasound system of claim 45, wherein said first and second data sets represent two dimensional ultrasonic images.

54. The ultrasound system of claim 45, wherein said first and second data sets represent portions of two dimensional ultrasonic images.

55. The ultrasound system of claim 45, wherein said first and second data sets represent three dimensional ultrasonic image volumes.

56. The ultrasound system of claim 45, wherein said first and second data sets represent portions of three dimensional ultrasonic image volumes.

57. In a medical diagnostic ultrasound system for acquiring a plurality of ultrasonic data sets of a human or animal, a method for estimating a transformation between: a first data set of said plurality of ultrasonic data sets, said first data set comprising a first plurality of data points, said first plurality of data points having a first arrangement characteristic in a first coordinate system, said first arrangement characteristic comprising distances, lengths and angles between one or more of said first plurality of data points; and a second data set of said plurality of ultrasonic data sets, said second data set comprising a second plurality of data points, said second plurality of data points having a second arrangement characteristic in a second coordinate system, said second arrangement characteristic comprising distances, lengths and angles between one or more of said second plurality of data points, said method comprising:

(a) calculating a rotation group, special orthogonal group of order 3 transformation between said first and second data sets;

(b) preserving said first arrangement characteristic in said second coordinate system using said transformation; and (c) approximating said second arrangement characteristic using said transformation.

58. The method of claim 57, wherein in (a) comprises calculating quaternions.

59. The method of claim 57, wherein in (a) comprises calculating orthonormal matrices.

60. An ultrasound system for medical imaging or therapy comprising:

a memory operative to store first and second ultrasonic data sets, each of which comprises a plurality of ultrasonic data, each of said data sets having an arrangement characteristic among each of said plurality of ultrasonic data, said arrangement characteristic comprising distances, lengths and angles between one or more of said plurality of ultrasonic data;

a processor coupled with said memory and operative to receive said data sets from said memory and compute a rotation group, special orthogonal group of order 3 transformation from said first data set to said second data set which preserves said arrangement characteristic of said first data set while approximating said arrangement characteristic of said first data set to said arrangement characteristic of said second data set.

61. The ultrasound system of claim 60, wherein said processor is operative to compute said transformation using quaternions.

62. The ultrasound system of claim 60, wherein said processor is operative to compute said transformation using orthonormal matrices.

63. An ultrasound system for medical imaging or therapy comprising:

means to store ultrasonic data into first and second data sets, each of said one or more data sets having an arrangement characteristic, said arrangement characteristic comprising distances, lengths and angles between one or more of said ultrasonic data;

means to process said first and second data sets from said means to store to compute a rotation group, special orthogonal group of order 3 transformation from said first data set to said second data set which preserves said arrangement characteristic of said first data set while approximating said arrangement characteristic of said second data set.

64. The ultrasound system of claim 63, wherein said processing means further comprises means to compute quaternions from said first and second data sets.

65. The ultrasound system of claim 63, wherein said processing means further comprises means to compute orthonormal matrices from said first and second data sets.

* * * * *

UNITED STATES PATENT AND TRADEMARK OFFICE
CERTIFICATE OF CORRECTION

PATENT NO.    : 6,306,091 B1
DATED         : October 23, 2001
INVENTOR(S)   : Thilaka S. Sumanaweera et al.

It is certified that error appears in the above-identified patent and that said Letters Patent is hereby corrected as shown below:

Title page,
Item [56], OTHER PUBLICATIONS, "J.D. Foley, A van Dam, S.K. Feiner and J.F. Hughes, eds" reference, delete "Practive" and substitute -- Practice --

Column 2,
Line 16, delete "set Once" and substitute -- set.  Once --
Line 29, delete "quatemions" and substitute -- quaternions --

Column 3,
Line 10, delete "ie.," and substitute -- i.e., --

Column 4,
Line 13, delete "comer" and substitute -- corner --
Lines 16 and 17, delete "comer" and substitute -- corner -- (both instances).

Column 5,
Line 9, delete "thereof The" and substitute -- thereof.  The --

Column 8,
Line 66, delete "quatemions. Quatemions" and substitute -- quaternions.  Quaternions --

Column 9,
Line 14, delete "X$_{p,i}$," and substitute -- x$_{p,i}$, --
Line 15, delete "Y$_{q,i}$," and substitute -- y$_{q,i}$, --
Line 38, delete "ith" and substitute -- i$^{th}$ --

Column 11,
Equation (7), delete "C$_p$" and substitute -- c$_p$ --
Line 49, delete "quatemions" and substitute -- quaternions --

UNITED STATES PATENT AND TRADEMARK OFFICE
CERTIFICATE OF CORRECTION

PATENT NO.    : 6,306,091 B1
DATED         : October 23, 2001
INVENTOR(S)   : Thilaka S. Sumanaweera et al.

It is certified that error appears in the above-identified patent and that said Letters Patent is hereby corrected as shown below:

Column 17,
Line 26, delete "quatemions." and substitute -- quaternions. --

Column 18,
Line 30, delete "quatemions." and substitute -- quaternions. --

Signed and Sealed this

Twenty-fifth Day of March, 2003

JAMES E. ROGAN
*Director of the United States Patent and Trademark Office*